US00PP16148P2

(12) United States Plant Patent
Olesen et al.

(10) Patent No.: US PP16,148 P2
(45) Date of Patent: Dec. 6, 2005

(54) MINIATURE ROSE PLANT NAMED 'POULPAR029'

(50) Latin Name: *Rosa hybrida*
Varietal Denomination: POULpar029

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 73 days.

(21) Appl. No.: 10/757,879

(22) Filed: Jan. 14, 2004

(51) Int. Cl.[7] ..... A01H 5/00
(52) U.S. Cl. ..... Plt./122
(58) Field of Search ..... Plt./122, 129

*Primary Examiner*—Anne Marie Grunberg
*Assistant Examiner*—June Hwu

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULpar029'.

SUMMARY OF THE INVENTION

The present invention constitutes a new and distinct variety of miniature pot rose plant which originated from a controlled crossing between the female parent 'KORstoffein', described and illustrated in U.S. Plant Pat. No. 11,242 dated Feb. 22, 2000, and the male parent, an unnamed seedling. The two parents were crossed and the resulting seeds were planted in a controlled environment. The new variety is named 'POULpar029'.

The new rose may be distinguished from its seed parent. 'KORstoffein', by the following combination of characteristics:

1. 'KORstoffein' petals which are Yellow-Orange Group 19D. The same of 'POULpar029' are Red Group 53A.
2. 'KORstoffein' has a petal count of 25 to 30. 'PUOLpar029' has 30 petals.

The new variety may be distinguished from its pollen parent, unnamed seedling created by the same inventors, by the following combination of characteristics:

1. The parent has a white flower color, whereas 'POULpar029' has a red flower color.
2. The parent plant has a petal count of 13 to 15, whereas the same of 'POULpar029' is 30.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULpar029' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULpar029' was selected by the inventors as a single plant from the progeny of the hybridization in 2000.

Asexual reproduction of 'POULpar029' by cuttings and traditional budding was first done by L. Pernille and Mogens N. Olesen in their nursery in Fredensborg, Denmark in 2001. This initial and other subsequent propagations conducted in controlled environments have demonstrated that the characteristics of 'POULpar029' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULpar029'. Specifically illustrated in the drawing:

FIG. 1.1; Stem showing branching and the attachment of leaves, buds, and peduncles;

FIG. 1.2; Flower bud closed, partially open, and open;

FIG. 1.3; Flower petals, detached;

FIG. 1.4; Sepals, receptacle, and pedicel;

FIG. 1.5; Bare stem exhibiting thorns;

FIG. 1.6; Juvenile leaves exhibiting anthocyanin and mature leaves.

DETAILED DESCRIPTION OF THE VARIETY

The following is a description of 'PUOLpar029', as observed in its growth in a field nursery in Jackson County, Oreg. Observed plants are 3 months of age, and were cultivated in 10 cm pots. Color references are made using The Royal Horticultural Society (London, England) Colour Chart, 1995, except where common terms of color are used.

For a comparison, several physical characteristics of the rose variety 'POULpar019', a rose variety from the same inventors described and illustrated in U.S. Plant Pat. No.

15,573 issued Feb. 22, 2005 are compared to 'POULpar029' in Chart 1.

CHART 1

| | 'POULpar029' | 'POULra019' |
|---|---|---|
| Petal color after opening outer petals. | Outer Side: Red Group 53B. Inner Side: Red Group 53A. | Outer Side: Red Group 53B. Inner Side: Red Group 53B. |
| Bloom diameter. | 35 mm. | 40 mm. |
| Petalage. | 30 petals. | 13 to 15 petals. |

Parents:

*Female seed parent.*—'KORstoffein'.

*Male pollen parent.*—Unnamed seedling.

FLOWER AND FLOWER BUD

Blooming habit: Continuous.

Flower bud:

*Size.*—Upon opening, 19 mm in length from base of receptacle to end of bud. Bud diameter is 10 mm.

*Bud form.*—Pointed ovoid.

*Bud color.*—As sepals unfold, petals are Red Group 53B to 53C. At ¼ opening petals are Red Group 53A.

*Sepals.*—Upper Surface: Color: Yellow-Green Group 147A to Green Group 143C. Anthocyanin at sepal apecies the color of Greyed-Orange Group 176A. Surface: Smooth and lightly pubescent. Lower Surface: Color: Yellow-Green Group 144A. Anthocyanin the color of Greyed-Orange Group 176A, located at sepal apecies. Texture: Smooth. Very light pubescence. Sepal Shape: Sepal apex is cirrhose. Base is flat at union with receptacle. Sepal Margin: 2 of the 5 sepals are entire. Medium to weak foliaceous appendages on three of the five sepals. Stipitate glands observed at margins. Size: 20 to 30 mm (l)×5 mm (w). With foliaceous appendages sepals are 10 mm wide.

*Receptacle.*—Surface: Smooth. Shape: Urn-shaped. Size: 5 mm (l)×5 mm (w). Color: Yellow-Green Group 144A.

*Peduncle.*—Surface: Prickles in medium quantity. Length: 40 to 45 mm. Color: Yellow-Green Group 144A. Strength: Upright and strong.

*Borne.*—Singularly.

Flower bloom:

*Fragrance.*—Very light floral scent.

*Duration.*—As a pot plant, flowers last 18 days.

*Size.*—For a 8–11 cm pot rose, flower diameter is 35 mm when open. Flower depth is 15 mm.

*Form.*—General shape is a rosette flower with many slightly overlapping petals of different sizes, arranged.

*Shape of flower when viewed from the side.*—Upon opening, upper part: Flat. Upon opening, lower part: Flattened Convex. Open flower, upper part: Convex. Open flower, lower part: Flattened Convex.

*Petalage.*—On average 30 petals under normal conditions with 2 petaloids.

Color:

*Upon opening, petals.*—Outermost petals: Outer side: Red Group 53A. Inner side: Red Group 53A to Red Group 46A. Innermost petals: Outer side: Red Group 53A. Inner side: Red Group 53A to Red Group 46A.

*Upon opening, basal petal spots.*—Outermost petals: Outer side: White Group 155A. Inner side: White Group 155A. Innermost petals: Outer side: White Group 155A. Inner side: White Group 155A.

*After opening, petals.*—Outermost petals: Outer side: Red Group 53B. Inner side: Red Group 53A. Innermost petals: Outer side: Red Group 53B. Inner side: Red Group 53A.

*After opening, basal petals spots.*—Outermost petals: Outer side: White Group 155A. Inner side: White Group 155A. Innermost petals: Outer side: White Group 155A. Inner side: White Group 155A.

*Petal color variations.*—Occasionally, the upper and under surfaces of petals and petaloids exhibit streaks the color of White Group 155A.

General tonality: On open flower Red Group 53A. No change in the general tonality at the end of the $10^{th}$ day. Afterwards, general tonality is Red Group 53A to 53B.

Petals:

*Petal reflex.*—Strongly on outer petals. Inner petals reflex only slightly.

*Margin.*—Entire, with a point in the center of the apex.

*Shape.*—Overall shape is deltoid. Apex is Rounded. Base is acute and slightly rounded.

*Size.*—Outer petal: 19 mm (l)×16 mm (w). Inner petal: 16 mm (l)×14 mm (w).

*Texture.*—Smooth.

*Thickness.*—Thick.

*Arrangement.*—Not Formal.

Petaloids:

*Quantity.*—2 on average.

*Shape.*—Irregular, deltoid.

*Color.*—Red Group 53A on outer side. Red Group 53A to Red Group 46A on inner side.

*Size.*—10 mm (l)×6 mm (w).

Reproductive organs:

*Pistils.*—Length: 4 mm. Quantity: 35 (actual count).

*Pollen.*—None observed.

*Anthers.*—Size: 2 mm long. Color: Yellow Group 12C. Quantity: 55 (actual count).

*Filaments.*—Color: Yellow Group 11C with intonations of Red Group 41C. Length: 4 to 5 mm.

*Stigmas.*—Inferior in location relative to the height of the anthers. Color: Greyed-Yellow Group 162D.

*Styles.*—Color: Greyed-Yellow Group 162D.

*Hips.*—None observed plants cultivated in 10 cm pots.

PLANT

Plant growth: Vigorous, compact, upright to bushy. When grown as a 8–11 cm pot plant, the average height of the plant itself is 18 cm and the average width is 10 cm.

Stems:

*Color.*—Young wood: Yellow-Green Group 146A. Older wood: Yellow-Green Group 146A. Internodal distance: 15 mm. Length of stems: 13 cm. Surface Texture: Young wood: Smooth. Older wood: Smooth.

Thorns:

*Incidence.*—7 to 9 mm per 10 cm of stem.

*Size.*—Average length: 4 mm.

*Color.*—Greyed-Red Group 179D.

*Shape.*—Linear.

Plant foliage: Normal number of leaflets on normal leaves in middle of the stem: 5 leaflets.

*Compound leaf size.*—75 mm (l)×41 mm (w).

*Quantity.*—8 leaves per 10 cm of stem.

*Color.*—Juvenile foliage: Upper Leaf Surface is Yellow-Green Group 144A. Lower Leaf Surface is Yellow-Green Group 147C with anthocyanic pigmentation the color of Greyed-Orange Group 177A to 176B. Mature foliage: Upper Leaf Surface is Green Group 147A. Lower Leaf Surface is Greyed-Green Group 194A. Anthocyanin intonation: Location: On plants grown under high light conditions, leaf margins of developing leaves and the undersides of juvenile foliage may exhibit anthocyanic intonations of Greyed-Orange Group 177A to 176B.

Plant leaves and leaflets:

*Stipules.*—Size: 15 mm (l)×4 mm (w). Shape: Linear, slightly broad based with outward extending apecies. Extensions are 5 mm in length. Margins: Finely serrated with stipitate glands. Color: Yellow-Green Group 146A.

*Petiole.*—Length: 23 mm. Color: Above: Yellow-Green Group 146B with intonations of Greyed-Orange Group 176A. Underneath: Yellow-Green Group 144B. Small prickles observed. Margins: Stipitate glands observed.

*Rachis.*—Size: 20 mm. Color: Above: Yellow-Green Group 146B with intonations of Greyed-Orange Group 176A. Underneath: Yellow-Green Group 144B. Small prickles normally located mid-way between leaflets. Margins: Stipitate glands observed.

*Leaflet.*—Size: 31 mm (l)×18 mm (w). Edge: Serrated. General Shape: Elliptical. Apex Shape: Acute. Base Shape: Round to acute. Texture: Smooth. Arrangement: Odd pinnate. Venation: Reticulate. Leaf Gloss: Moderately glossy.

Disease resistance: Average resistance to Powdery mildew, Downy mildew, black spot, and Botrytis under normal growing conditions in a greenhouse located in Burlington, Ontario.

It is claimed:

1. A new and distinct variety of rose plant of the miniature class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

* * * * *

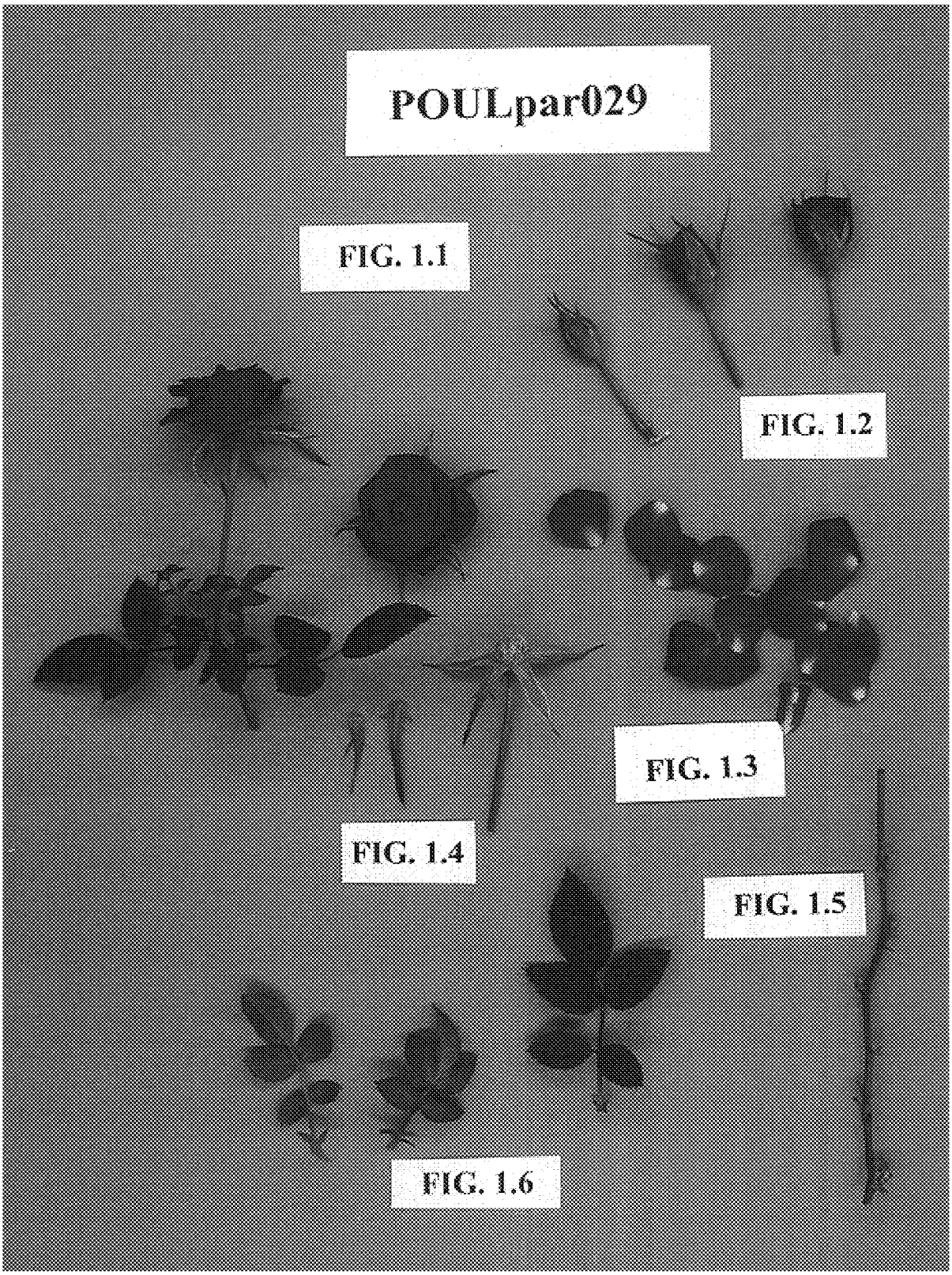
POULpar029
FIG. 1.1
FIG. 1.2
FIG. 1.3
FIG. 1.4
FIG. 1.5
FIG. 1.6